United States Patent [19]

Reid et al.

[11] Patent Number: 4,580,440

[45] Date of Patent: Apr. 8, 1986

[54] METHOD OF DETECTING A CONTRABAND SUBSTANCE

[75] Inventors: Neil M. Reid; William R. Davidson, both of Thornhill, Canada

[73] Assignee: British Aerospace Public Company Limited, Bracknell Division, Bracknell, England

[21] Appl. No.: 631,953

[22] Filed: Jul. 17, 1984

[51] Int. Cl.⁴ .......................... G01N 1/22; G01N 33/22
[52] U.S. Cl. ............................................. 73/23; 73/864
[58] Field of Search ..................................... 73/23, 864

[56] References Cited

U.S. PATENT DOCUMENTS

| | | | |
|---|---|---|---|
| 3,748,905 | 7/1973 | Fletcher et al. | |
| 3,942,357 | 3/1976 | Jenkins | 73/23 |
| 3,998,101 | 12/1976 | Bradshaw et al. | 73/864 |
| 4,045,997 | 9/1977 | Showalter et al. | 73/23 |
| 4,202,200 | 5/1980 | Ellson | 73/23 |

FOREIGN PATENT DOCUMENTS 1360317 7/1974 United Kingdom .
1497436 12/1978 United Kingdom .

Primary Examiner—Stewart J. Levy
Assistant Examiner—Joseph W. Roskos
Attorney, Agent, or Firm—Rogers, Bereskin & Parr

[57] ABSTRACT

A method of detecting contraband substances in freight cargo containers in which the container is agitated to disturb particulates therein, and air containing such particulates is then sampled and the particulates collected. The collected particulates include naturally occurring particulates which have absorbed vapors of the contraband substance during the entire time that the container has been closed, and also include particulates of the contraband substance itself. The collected particulates are heated to drive off vapors indicative of the contraband substance and the vapors are analyzed in a mass analyzer.

23 Claims, 13 Drawing Figures

METHOD OF DETECTING A CONTRABAND SUBSTANCE

FIELD OF THE INVENTION

This invention relates to a method of detection for detecting contraband such as drugs, alcohol, firearms and explosives in containers.

BACKGROUND OF THE INVENTION

Much cargo is presently carried in cargo containers. Such cargo containers can be quite large (from 10 feet to 50 feet in length or more). When such containers are unloaded from ships, rail cars or aircraft, at ports of entry into a country, they should in theory be inspected by customs authorities. However, because the volume of such container traffic is high, and because each container may be loaded with sealed boxes, drums and the like, it is impossible in practice to inspect the contents of each container. In fact, because of the high volume of such traffic, there may be only a few minutes available to inspect each container.

X-ray examination of such containers has been proposed. Such x-ray examination is capable of detecting certain types of contraband, such as firearms, but it is not capable of detecting other kinds of contraband, such as drugs, alcohol and explosives if such substances are appropriately packaged.

Attempts have therefore been made to detect contraband such as drugs, alcohol, firearms and explosives by other means, such as by detecting vapors emitted by these items. However, these methods have resulted in high false alarm rates and unreliable detection of the substances, for various reasons. Among the reasons are the extremely low vapor pressures of many of the substances which are to be detected. In addition, although many contraband substances emit vapors from their breakdown products or from products associated with their manufacture, such vapors may also be emitted by other industrial products, resulting in false alarms. The unnecessary inspections resulting from the false alarms can, due to their frequency, cause a breakdown of the entire detection process.

BRIEF SUMMARY OF INVENTION

The inventors have discovered that many contraband substances which are to be detected, such as drugs and explosives, and which may have extremely low vapor pressures, emit (even when packaged) particulates which then are present in the cargo container in which such contraband is being transported. The particulates are emitted in various ways. When the contraband is not wrapped the particulates may be emitted through simple mechanical abrasion. When the contraband is packaged, particulates may be emitted through pin holes in the packaging in which the contraband is wrapped, or they may be present on the packaging because the person who wrapped the contraband touched the packaging after touching the contraband. Alternatively, they may be present on the packaging because of a dusty environment in the location where the contraband was wrapped.

It has been discovered that the particulates emitted from the contraband escape into the cargo container in which the contraband is transported. Some of such particulates remain airborne within the container and some settle on surfaces in the container. Such surfaces may include the surfaces of the container itself or packages in the container. The particulates may also settle on or agglomerate with dust (i.e. other particulates) located in the container. In addition vapors emitted from the contraband are absorbed over a period of time by non-contraband particulates in the container, providing a concentration effect. Therefore it has been discovered that if the container itself is agitated prior to inspection to cause particulates therein to become airborne, and if the air in the container is then sampled and the particulates in such air collected, such particulates will frequently contain particulates from the contraband or vapors absorbed from the contraband. The collected particulates are then analyzed to detect the presence of the contraband substance. The invention therefore provides a new and unusual information channel for detecting the presence of contraband.

In its broadest aspect the invention provides a method of detecting a contraband substance in a container, said method comprising the steps of:

(1) ensuring that at least some of the particulates present on surfaces in said container have been agitated substantially immediately before step (2) below to cause at least some of said particulates to become airborne, (2) sucking air containing said particulates into a collector and collecting at least some of said particulates in said air, (3) heating said collected particulates to desorb vapor of said contraband substance therefrom, and (4) analyzing said vapor for said contraband substance.

BRIEF DESCRIPTION OF THE DRAWINGS

The invention will be described in more detail with reference to the accompanying drawings in which.

DETAILED DESCRIPTION OF PREFERRED EMBODIMENTS OF THE INVENTION

Figure 1:
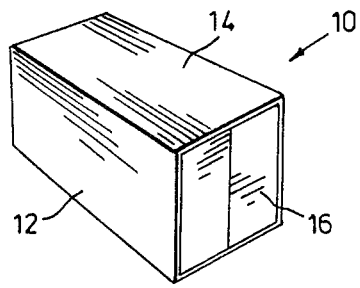
FIG. 1 is a perspective view of a typical cargo container in which contraband may be transported.

Reference is first made to FIG. 1, which shows a typical cargo container 10 having sides 12, a top 14 and doors 16 located at one end thereof. The cargo container 10 may be a standard forty foot container of the kind transported by ship and then by truck or rail from the port at which the ship loads or unloads, or it may be an air cargo container, or it may simply be a large trailer of the kind pulled by truck tractors for highway use. Such containers may be used to carry contraband such as drugs, alcohol, firearms or explosives. Because of the high volume of traffic in such containers, it is not practical to unload and inspect the contents of each container.

High energy x-ray facilities have been proposed to x-ray such containers. A typical such high energy x-ray facility is shown at 18 in FIG. 2. As there shown, the containers are transported on a conveyor 20, which may be a belt conveyor or a roller conveyor, through a thick-walled concrete building 22. In the building 22 an x-ray source 24 transmits high energy x-rays 26 through the container 10 to an imaging device 28. The imaging device transmits to a screen (not shown), the image produced by the x-rays, so that the operator may view the image and detect the presence of certain kinds of contraband. Thick radiation proof doors 29 seal the x-ray source during the x-ray process to prevent escape of dangerous x-rays.

The high energy x-ray facility 18 can detect the presence of certain objects, such as firearms, even through relatively thick metal walls. However, it is not capable of detecting contraband such as explosives and drugs when these are appropriately packaged. The applicant's invention is particularly suited to be used in combination with the x-ray facilities shown, particularly when the conveyor 20 is adapted to agitate the container 10 as will be described.

Restricted drugs such as heroin and cocaine are usually transported in the form of their salts, typically hydrochloride or sulphate salts. These salts have an extremely low vapor pressure, which may be as low as $10^{-7}$ torr. Cannabis and many explosives have a similarly low vapor pressure. If the vapor from small quantities of such contraband substances were to be detected in a container, it would be necessary to sample the air in the container at least for several hours, if not more, and then to concentrate that air to obtain a sufficiently large quantity of the contraband vapor for detection.

Many types of contraband substances emit more volatile breakdown or related products. For example, explosives may emit cyclohexanone, which is a solvent used during the manufacturing process. Heroin may emit vapors of acetone (a solvent used therein) and acetic acid (a breakdown product of heroin) or of caffeine, which is a "cutting" agent used in heroin. Cocaine may emit vapors of acetone (a solvent) or methylbenzoate (a breakdown product) or of lidocaine (a "cutting" agent used in cocaine). Cannabis may emit pinene or sesquiterpenes, which are volatile non-active ingredients thereof. Table I at the end of this description lists these chemical or contraband signatures and shows their relative volatilities.

Unfortunately many of the vapors of the materials listed in Table I may also be emitted by other commercial materials, resulting in a high false alarm rate. In addition, the vapor pressure of many of the substances is extremely low. In addition, the vapor pressure of all substances falls when the temperature is relatively low.

As previously mentioned, it is found that most contraband substances (except of course for liquids) emit particulates. This is partly because virtually all packaging contains microscopic pinholes through which the particulates may pass, and partly because of contamination of the substance on the packaging itself. The contamination on the packaging may result from various factors, e.g. the person who wrapped the contraband may have touched the contraband and then the packaging, or airborne contraband particles at the wrapping location may have settled on the packaging, or non-contraband dust particles at the wrapping location which may have absorbed and concentrated vapors from the contraband may have settled on the packaging. In addition the contraband substance (including liquids) while in the container may emit vapors, both of its active ingredient and of other characteristic products associated with it, although often at very low pressures. These vapors usually diffuse through the packaging in which the contraband is located.

Most cargo containers contain dust, i.e. particulates, of various kinds. The dust particles may for example be fibrous (e.g. lint from paper, cardboard, cloth, and the like), silicacious (e.g. sand and rock dust) and carbonaceous (e.g. soot, skin particles and the like). Many of these dust particles act as good natural absorbers of the vapor emitted by the contraband. In addition many natural dust particles are relatively sticky and may tend to agglomerate with particulates of the contraband itself.

The particles of interest may range in use from $10^{-7}$ meters to $2\times 10^{-6}$ meters (smoke particles) and from $2\times 10^{-6}$ meters to $10^{-3}$ meters (airborne dust particles) and even larger for such particles as lint.

The time between when a cargo container is loaded and when it must be inspected is usually at least a day or several days and can be much more. This allows considerable time for the dust particles in the container to absorb and in effect to concentrate vapors from contraband in the container. It also allows considerable time for particulates of the contraband to be emitted and to float within or settle on surfaces within the cargo container.

As the container experiences its voyage, the resultant vibration may increase the number of natural particles available to act as absorbers and also increases the number of contraband particles emitted. The vibration also causes more even distribution of all these particles within the container. Temperature changes within the container, caused by heating and cooling as the ambient environment changes, also increase the distribution and mobility of particles within the container.

Therefore, according to the invention particulates in the container are collected and analyzed for the presence of contraband. The particulates are collected by sampling the air within the container. To ensure that a sufficient quantity of particulates is collected, the container is agitated immediately or at least shortly prior to sampling the air therein.

Figure 3:
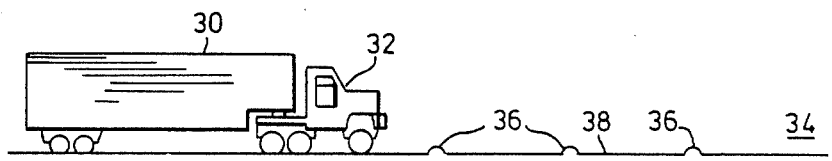
FIG. 3 is a diagrammatic side view of a road arrangement to ensure agitation of truck transported containers.

The agitation may be performed in several ways. If the container 10 is the trailer 30 (FIG. 3) of a tractor-trailer combination 32 which has been driven to the sampling location 34, then frequently no additional agitation will be required since considerable agitation occurs during the driving process. However, if necessary, a bumpy road surface or "speed bumps" 36 may be provided in the portion of the road 38 over which the trailer must be driven as it travels to the inspection location.

Figure 4:
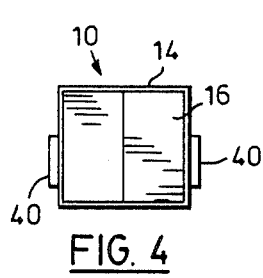
FIG. 4 is a front view of a cargo container having vibration transducers connected thereto.

Alternatively, a vibrating device 40 (FIG. 4) may be placed against the sides or top of the container 10 to vibrate the container. The vibrating device 40 may be an ordinary direct mechanical vibrator or may be a sonic or ultrasonic transducer, to agitate the contents of the container. If desired two such vibrating devices 40 may be used, one placed against each side of container 10 and preferably near the bottom of the container, to maximize the vibration accelerations applied to the cargo and other surfaces within the container.

Figure 2:
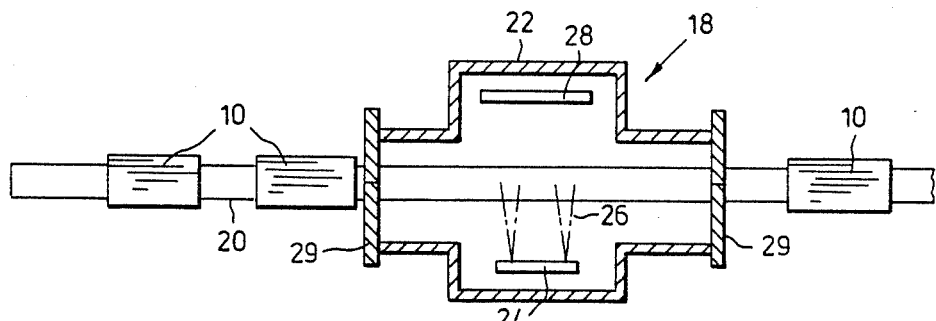
FIG. 2 is a plan view of a typical prior art x-ray installation used to x-ray cargo containers.
Figure 5:
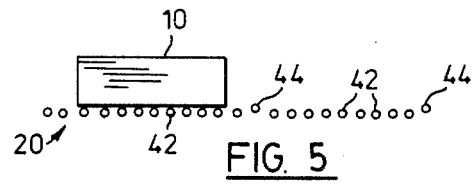
FIG. 5 is a diagrammatic side view of a roller conveyor having a cargo container thereon.
Figure 6:
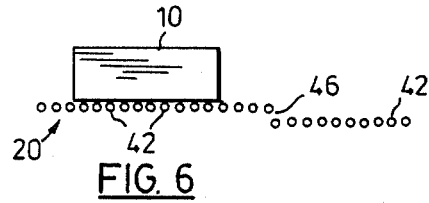
FIG. 6 is a diagrammatic side view of another roller having a cargo container thereon.

If the container 10 is travelling on a roller conveyor such as that shown at 20 in FIG. 2, then the rollers 42 (FIG. 5) of the conveyor may be staggered as shown in exaggerated form at 44 or may be made of different diameters, to bump the container immediately prior to its movement into the air sampling location 34. Sufficient propulsive force (either by gravity or by powered rollers) is provided to ensure continued movement of the container 10. Alternatively, the conveyor 20 may contain a small drop indicated at 46 in FIG. 6 so that the container actually falls several inches to stir up the dust within the container.

Figure 7:
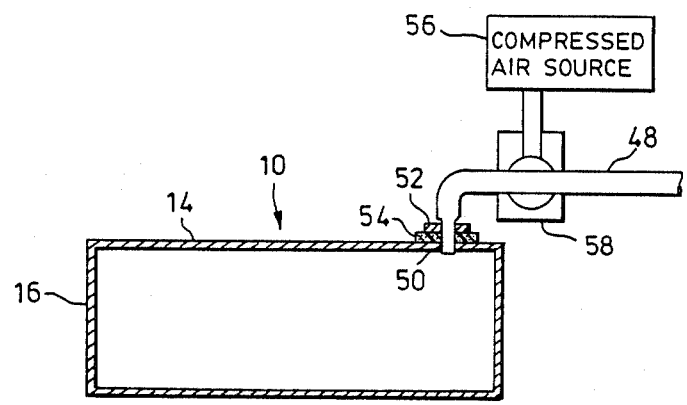
FIG. 7 is a diagrammatic view of a sampling line connected to a cargo container.

The air within the container 10 is sampled through a sampling line 48 as shown in FIG. 7. To perform the sampling, a hole 50 is bored in the roof of the container and the sampling line 48 inserted therethrough. Typically a two-inch hole will be bored through the container roof 14 and the sampling line 48 will include a collar 52 and a foam seal 54 beneath the collar 52. The collar and seal are pressed against the outside of the container roof 14 adjacent the hole 50, to seal the hole around the sampling line 48 against movement of air therethrough. After the sampling has been completed and the sampling line is removed, a plug (not shown) is fitted into the hole 50 to seal it. The plug may contain a valve so that when the container is next inspected, the sampling line 48 can simply be connected to the valve.

If desired, instead of or in addition to mechanically vibrating the container, a blast of high-pressure air may be injected through the sampling line 48 from a source 56 of compressed air, directed through a valve 58, in order to agitate dust within the container. Alternatively, a separate high pressure air line may be inserted into the hole 50 to agitate dust, such line can then be removed and replaced by the sampling line. However this is not preferred because of the potential for particle loss during the disconnect-connect cycle.

As shown in FIG. 7, the hole 50 is bored and the sampling line 48 is inserted into the container 10 at a location remote from the doors 16. Doors are a prime source of air leakage into the container. When the sampling line 48 is placed as far as possible from the doors, and air is sucked into the sampling line, a flow of air is set up through the container from the doors to the sampling line, carrying dust in the container with such flow.

Where the container is an open-backed or tarpaulin covered truck body, high pressure air from a compressed air source may be injected into one end of the container at the same time as an air sample is being withdrawn from the other end of the container, in order to set up a better air flow containing particulates. Where the container is a closed cargo container, its doors may nevertheless have sufficient gaps at their seals so that an air hose can be pressed against or through such gaps, or through the rubber seals around the gaps, to inject air during the sampling process.

Figure 8:
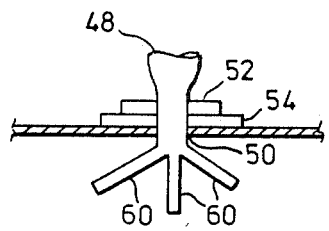
FIG. 8 is a diagrammatic view of a modified sampling line connected to a cargo container.

If desired, in order to improve the distribution of air collection within the container, the sampling line may contain tentacles 60 as shown in FIG. 8. The tentacles 60 tend to fan out when the sampling line is inserted through the hole 50. The tentacles 60 will normally be relatively short and may include an expansion mechanism (not shown) so that they are directed in different directions as they move below the roof of the container. There is usually a space of at least six to twelve inches between the roof of a container and the top of the cargo therein to allow space for such tentacles.

Figure 9:
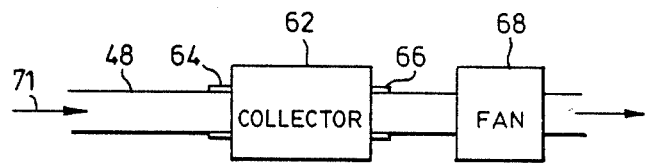
FIG. 9 is a diagrammatic view of a collector connected to the sampling line of FIGS. 7 or 8.

The sampling line 48 typically extends to a sample collector 62 as shown in FIG. 9. Air is drawn from line 48 into an inlet 64 of the collector and through collector outlet 66 to atmosphere by an air pump 68.

The line 48 will often be of a substantial length. When vapors are being detected, it has been found that molecules of a medium molecular weight compound can lose 50% or more of their number in a line 48 of between 5 and 10 meters in length. These molecules tend to diffuse rapidly to the walls of the line 48 where they are held by molecular binding forces. This loss not only reduces the signal to be analyzed but also causes undesirable memory effects since molecules which are absorbed or trapped on the walls of line 48 may be released at inopportune times. (To reduce but not eliminate this problem, the walls of line 48 may be heated.) The inventors have however discovered that particulates will travel much further along a line, even an unheated line, with much lower losses than molecules. The particulate losses in a 10 meter line are minor and even a 100 meter long line 48 can be used if needed. The particulate losses are lower because the particulates diffuse much more slowly than do molecules to the walls of the line 48. These particulates which do reach the walls of the line 48 are more likely than molecules to be dragged off the walls because of the greater projection of the particulates into the shear layer adjacent the wall. This enables the collector system to be described to be at a greater distance from the container where necessary. Since it is often difficult to bring sophisticated equipment close to the container being inspected, this aids the establishment of a practical inspection system. At the same time undesirable memory effects in the line 48 are avoided.

Preferably the diameter of line 48 is increased immediately outside the hole 50, e.g. to between four inches and eight inches. Air is sucked through the line 48 at the maximum possible flow rate, both to obtain the largest possible quantity of particulates, and to reduce the likelihood that particulates will settle in the line 48.

The line 48 should be smooth walled, without sharp bends or sudden sharp expansions or contractions, all of which tend to trap particles. Preferably no bend should be sharper than about five times the internal diameter of the line 48. Preferably the bends should be ten internal line diameters or more. In addition, at those locations where the internal diameter of the line is increased, the increase in internal diameter preferably should not be at a rate greater than about a 7 degree half angle cone. With more abrupt expansions, the flow in the line is more likely to separate from the line wall and form a turbulent region with backflow, which can cause settling and undesired memory effects. Contractions in the internal diameter of the line do not normally cause flow separation and can be more abrupt but should be smoothly contoured and moderately gradual. Further, the roughness of the internal surface of the wall of line 48 should preferably not be greater than about 1% of the internal line diameter. The line 48 may be made from the plastic known under the trade mark TEFLON and may be heated if trace vapors are also to be conducted through the line.

Figure 10:
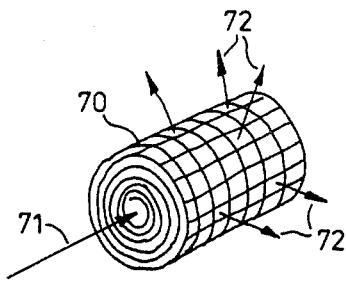
FIG. 10 is a perspective view of a collector element.

The collector 62 performs the function of collecting, i.e. trapping particulates located in the air stream entering the collector. This can be accomplished in various ways. For example the collector 62 may be a conventional cyclone. Alternatively, it may be a rolled coil 70 of wire mesh as shown in FIG. 10. The air stream 71 in the line 48 enters the center of the coil 70 and travels radially therethrough as indicated by arrows 72 (such like an automobile air filter). The wire mesh coil 70 is coated with an appropriate sticky substance such as a light oil. Particulates in the air stream are collected on the sticky wire surfaces of the collector during the air sampling process. Other forms of collector may also be used.

Figure 11:
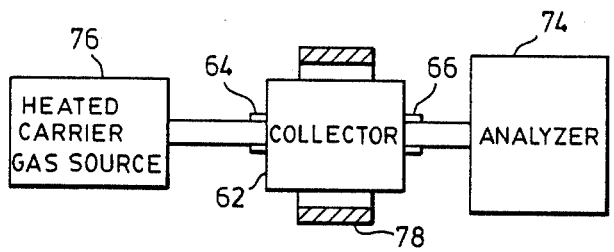
FIG. 11 is a view of a collector connected to an analyzer.

After the particulates have been collected, the collector 62 (which can preferably be quickly plugged into and unplugged from line 48) is removed from line 48 and connected to an analyzer 74 (FIG. 11) to be described. A source 76 of heated carrier gas is plugged into the collector inlet 64. In addition the collector 62 itself can be heated by a heater, for example an induction heater 78. This process rapidly releases vapors absorbed by the trapped particulates and the vapors are carried over a short period of time (e.g. 30 seconds) into the analyzer 74 for analysis. The heating is controlled so as not to destroy the oil coating on the mesh coil 70.

The oil referred to above should be an oil of low volatility when heated and one which does not oxidize when heated. If appropriate oils are used, the compounds of interest may dissolve from the particulates into the oil, which acts as a solvent, and are then evaporated from the oil into the heated carrier gas stream. Stationary phase oils or gums used in conventional gas chromatography columns have been found suitable. These oils are generally organo-silicone polymers ot other non-volatile organic polymers. For example an organosilicon polymer oil sold under the designation OV-275 by several suppliers, including Alltech Associates of Deerfield, Ill., U.S.A. has been fround particularly suitable for explosives. A similar oil sold under the designation OV-17 by the same suppliers has been found particularly suitable for cocaine and heroin.

Because the degassing of the particulates and the movement of the resultant vapor into the mass analyzer occurs in a shorter time than the step of collecting the particulates, and because the volume of vapor released into the mass analyzer is much smaller than the volume of air collected, a large concentration effect is achieved. For example, if 100 cubic liters of air per second are collected from the container for 30 to 60 seconds, then 3000 to 6000 liters of air are collected. If the carrier gas flow from the collector 62 to the analyzer 74 is 0.1 liters per second for 10 seconds (1 liter), then a very large concentration effect is achieved, dependent of course in part on the efficiency with which particulates are collected. A further concentration effect is achieved because of the collection both of particulates ambient in the container which have had a long time to absorb contraband volatiles, and of particulates of the contraband itself which have had a long time to migrate about the container.

Figure 12:
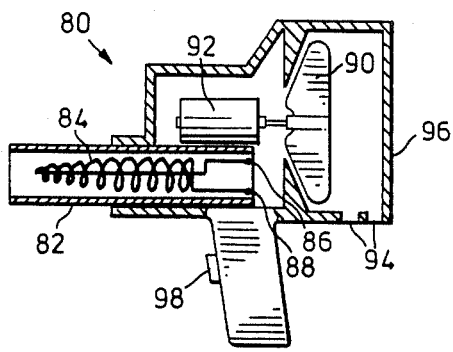
FIG. 12 is a cross-sectional view of a typical hand held collector.

If desired a hand held collector may be used in place of or in addition to the collector 62 and sampling line 48. The hand held collector may be for example of the kind shown at 80 in FIG. 12. Collector 80 includes a removable glass tube 82 having a spiral wound wire collector coil 84 therein having two contacts 86, 88. Air is sucked into tube 82 by a fan 90 driven by a motor 92, and exits through holes 94 in casing 96. The motor 92 is driven by batteries (not shown) and is turned on by a trigger switch 98. Thus the collector 80 can be brought to a container or trailer which is to be inspected more closely. After a sample has been collected, tube 82 with the coil 84 therein is removed and plugged into the analyzer 74 like the collector 62. However a source of electrical current (not shown) may be connected to contacts 86, 88 to heat the wire coil 84 like a filament, to drive off vapors absorbed by particulates trapped in the coil.

Figure 13:
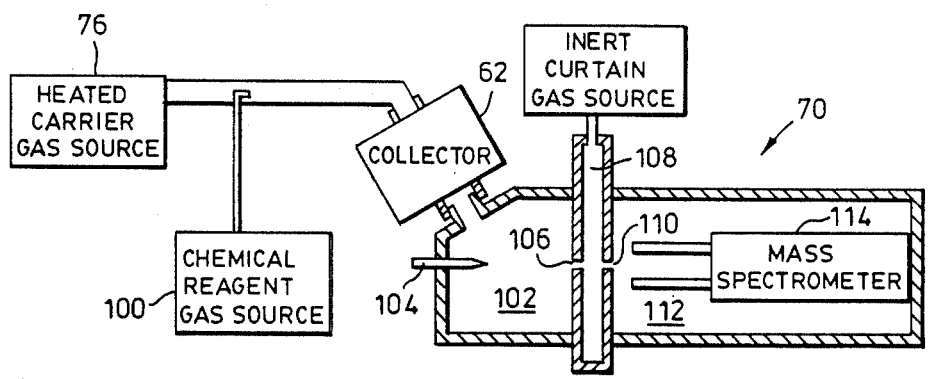
FIG. 13 is a diagrammatic view of a mass analyzing system used in connection with the method of the invention.

The analyzer 70 may be a mass analyzer such as that sold under the trade mark TAGA by Sciex Division of MDS Health Group Limited of Thornhill, Ontario, Canada, as shown in FIG. 13. Typically the heated carrier gas from source 76 will be directed past a chemical reagent gas source 100 and a mixture of both gagses will travel through the collector 62 into the inlet section 102 of the analyzer 70 for ionization. The inlet section 102 will include an ionizing source such as a corona discharge needle 104 which provides a corona discharge to ionize trace substances of interest. The resultant ions are then pulled by an electric field through an orifice 106 into a gas curtain chamber 108 and then through another orifice 110 into a vacuum chamber 112 where they anter a mass spectrometer 114.

The gas curtain section 108, described in U.S. Pat. No. 4,023,398 issued on May 13, 1977 to J. B. French et al, provides an inert curtain gas (such as argon) which effuses from orifice 106 into chamber 102, i.e. countercurrent to the flow of ions into the orifice 106. The curtain gas thus prevents particulates from entering and clogging the orifices 106, 110 and allows only the ions to travel into the vacuum chamber 112. The curtain gas enters the vacuum chamber 112 and may be cryopumped or pumped by an ordinary vacuum pump to establish a vacuum in chamber 112. The gas curtain is particularly useful in the present invention since the gas flow into the analyzer tends to be particulate laden (which is the opposite of what is normally desired) because of particulates carried out of the collector and into the analyzer. Such particles would rapidly clog an unprotected orifice.

The method of the invention may also be used with substances such as alcohol which do not emit particulates. Where there are very small quantities of vapor present, the absorption of such vapor by particulates in the container over a period of days provides a concentration effect which increases the reliability of detection when the method of the invention is used. However the invention is primarily applicable to the detection of contraband substances which emit particulates.

Although the steps of collecting the particulates and then heating them have been shown as discrete batch-type steps, if desired a continuous process can be used in which the collected particulates are continuously advanced to a heating location and heated to desorb absorbed vapors.

The term "container" as used herein is meant to include any kind of container in which contraband may be transported, including without limitation cargo containers, trailers, trucks, autos, aircraft, luggage, trunks, boxes, letters and other mail. In the case for example of some luggage and other resilient containers, air may be sampled from the luggage container simply by compressing the luggage container.

TABLE I

| CONTRABAND | CHEMICAL OR CONTRABAND SIGNATURES VOLATILE COMPONENTS | | | | SOURCES OF PARTICULATES |
|---|---|---|---|---|---|
| | HIGH VOLATILITY (approximately $10^6$ dynamic range from left to right) | | | LOW VOLATILITY | |
| EXPLOSIVES | | | | | |
| INDUSTRIAL | EGDN (ethylene glycol dinitrate) | | | NG (nitroglycerine) | Microscopic particles of EGDN and NG produced during manufacture and packaging and dust particles contaminated by NG and/or EGDN. |
| MILITARY | CYCLOHEXANONE (Solvent used in plastic explosives) | | DNT (dinitrotoluene) | TNT (trinitrotoluene) | Microscopic particles of TNT and DNT and contaminated dust particles. |
| DRUGS | | | | | |
| COCAINE | ACETONE (solvent) | METHYL-BENZOATE (breakdown product) | LIDO-CAINE ("cutting" agent) | COCAINE (base) | Microscopic particles of Cocaine hydrochloride, the common salt form, Cocaine base and Lidocaine and contaminated dust particles. |
| HEROIN | ACETONE (solvent) | ACETIC ACID (breakdown product) | | CAFFEINE ("cutting" agent) | Microscopic particles of Heroin hydrochloride and/or sulphate, the common salt forms, and Caffeine and contaminated dust particles. |
| SPEED (amphetamines) | DIMETHYLAMPHETAMINE (active compound) | | | | Dust particles contaminated with dimenthylamphetamine. |
| CANNABIS | | PINEN, SESQUITERPENES (non-active ingredients) | | TETRAHYDRO-CANNABINOL (active compound) | Microscopic particles of Tetrahydrocannabinol Cannabadiol and Cannabinol and contaminated dust particles. |
| BARBITUATES | | | | | Microscopic dust particles of Barbital and Barpental. |
| ALCOHOL | | | | | |
| SPIRITS WINES BEERS | ETHANOL (alcohol) | ACETIC ACID (breakdown product) | | | No particles of a direct nature. |

We claim:

1. A method of detecting a substance in a container, said substance being of the kind which emits particulates or which emits vapors that can be retained by non-volatile particulates, said method comprising the steps of:
   (1) ensuring that said container has been agitated substantially immediately before step (2) below to cause at least some of the particulates present within said container to become airborne within said container,
   (2) sucking air containing said airborne particulates from said container into a collector without vacuuming any surfaces in said container, and collecting at least some of said particulates in said air, such collection being without heating said particulates sufficiently to release vapor of said substance therefrom,
   (3) then after collecting said particulates, rapidly heating said collected particulates sufficiently to release vapor of said substance therefrom, and
   (4) analyzing said vapor for said substance.

2. A method according to claim 1 wherein said container is a freight cargo container.

3. A method according to claim 2 wherein said agitation is carried out by directing an air jet into said container.

4. A method according to claim 3 wherein said step of sucking air from said container is performed by introducing a sampling line into said container and wherein said agitation step is performed by blowing said air jet through said sampling line.

5. A method according to claim 2 wherein said step of sucking said air is performed by introducing a sampling line having a number of tentacles at its end into said container so that air is sucked from a number of different directions into said sampling line.

6. A method according to claim 2 wherein said container is carried on a conveyor into a high energy x-ray examination facility and said agitation is performed by said conveyor.

7. A method according to claim 1 wherein said agitation is performed by dropping said container through a short distance.

8. A method according to claim 1 wherein said agitation is carried out by connecting a vibration transducer to said container.

9. A method according to claim 8 wherein said transducer is an ultrasonic transducer.

10. A method according to claim 1 wherein said agitation step is performed by agitating said container on a conveyor which simultaneously transports said container.

11. A method according to claim 1 wherein said container has a door at one end and wherein said step of sucking air is performed at a location remote from said one end.

12. A method according to claim 1 wherein air is blown into said container at one location and said step of sucking said air is performed at a location remote from said one location.

13. A method according to claim 1 wherein said collection step includes the step of directing air from said container over a sticky collector surface to trap said particulates on said surface.

14. A method according to claim 13 wherein said step of heating includes the step of heating said collector surface.

15. A method according to claim 1 wherein said contraband substance is heroin.

16. A method according to claim 1 wherein said contraband substance is cocaine.

17. A method according to claim 1 wherein said contraband substance is cannabis.

18. A method according to claim 1 wherein said contraband substance is an explosive substance.

19. A method according to claim 1 wherein said step (4) is performed by flowing said desorbed vapor together with a carrier gas into an ionizing chamber, forming ions from said desorbed vapor, conducting said ions through a first orifice and through a gas curtain and through a second orifice into a vacuum chamber containing a mass analyzer, and causing said gas curtain to effuse from said first orifice countercurrent to the flow of said ions to prevent particulates entrained in said desorbed vapor and said carrier gas from clogging said orifice.

20. Apparatus for detecting a substance in a freight container, said substance being of the kind with emits particulates or which emits vapors that can be retained by non-volatile particulates, said apparatus comprising:
(1) collection means for collecting particulates,
(2) suction means for sucking air, and airborne particulates in said air, from the volume of air within said container into said collection means to collect at least some of said airborne particulates from said container in said collection means,
(3) means operable after collection of said airborne particulates for rapidly heating said collected particulates sufficiently to release vapors of said substance therefrom,
(4) analyzer means for analyzing said vapors,
(5) and means for conveying vapors released from said particulates from said collection means into said analyzer means for analysis thereof.

21. Apparatus according to claim 20 and including means for agitating said container to increase the number of particulates which are airborne within said container.

22. Apparatus according to claim 21 wherein said suction means includes a long air line having essentially no bends having a radius less than about five times the internal diameter of the line, and having no increases in the internal diameter therein at a rate greater than about a 7 degree half angle cone, and having an internal surface roughness which does not exceed about 1 percent of the internal diameter of the line.

23. Apparatus according to claim 22 wherein said line is at least about 10 meters in length.

* * * * *